United States Patent [19]

Church

[11] 4,414,978
[45] Nov. 15, 1983

[54] UNIVERSAL PROGRAMMER FOR OPERATING IMPLANTABLE DEVICE REED SWITCH

[75] Inventor: Victor E. Church, Hornsby Heights, Australia

[73] Assignee: Telectronics Pty. Ltd., Lane Cove, Australia

[21] Appl. No.: 296,458

[22] Filed: Aug. 26, 1981

[51] Int. Cl.³ .............................................. A61N 1/38
[52] U.S. Cl. ............................................. 128/419 PG
[58] Field of Search .................... 128/1.4, 1.5, 419 P, 128/419 PG, 419 PS, 419 PT

[56] References Cited

U.S. PATENT DOCUMENTS

| | | | | |
|---|---|---|---|---|
| 1,120,964 | 12/1914 | Neel | ..................................... | 128/1.5 |
| 2,897,411 | 7/1959 | Brown et al. | ......................... | 128/1.4 |
| 3,311,111 | 3/1967 | Bowers | ......................... | 128/419 PG |
| 3,518,997 | 7/1970 | Sessions | ......................... | 128/419 PS |
| 3,800,801 | 4/1974 | Gaillard | ......................... | 128/419 PT |
| 3,945,387 | 3/1976 | Adams | ......................... | 128/419 PG |

Primary Examiner—William E. Kamm
Attorney, Agent, or Firm—Gottlieb, Rackman & Reisman

[57] ABSTRACT

There is disclosed on external programmer for use with heart pacers of two different types. Depending on the reed orientations in the two types of pacers, the magnetic flux generated by the programmed has to be in one of two orthogonal directions through the pacers. A pair of parallel coils is provided. A switching circuit switches the current direction through one of the coils so that the two coil fluxes aid or oppose each other, thus giving rise to orthogonal fluxes through pacers to be adjusted. A pacer of either type can thus be adjusted without the physician having any concern for the reed/-programmer orientations.

21 Claims, 5 Drawing Figures

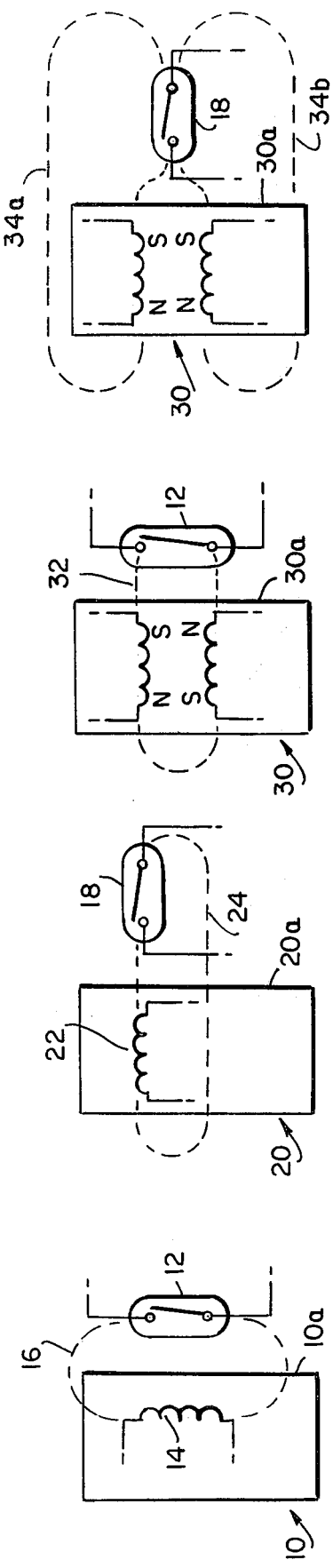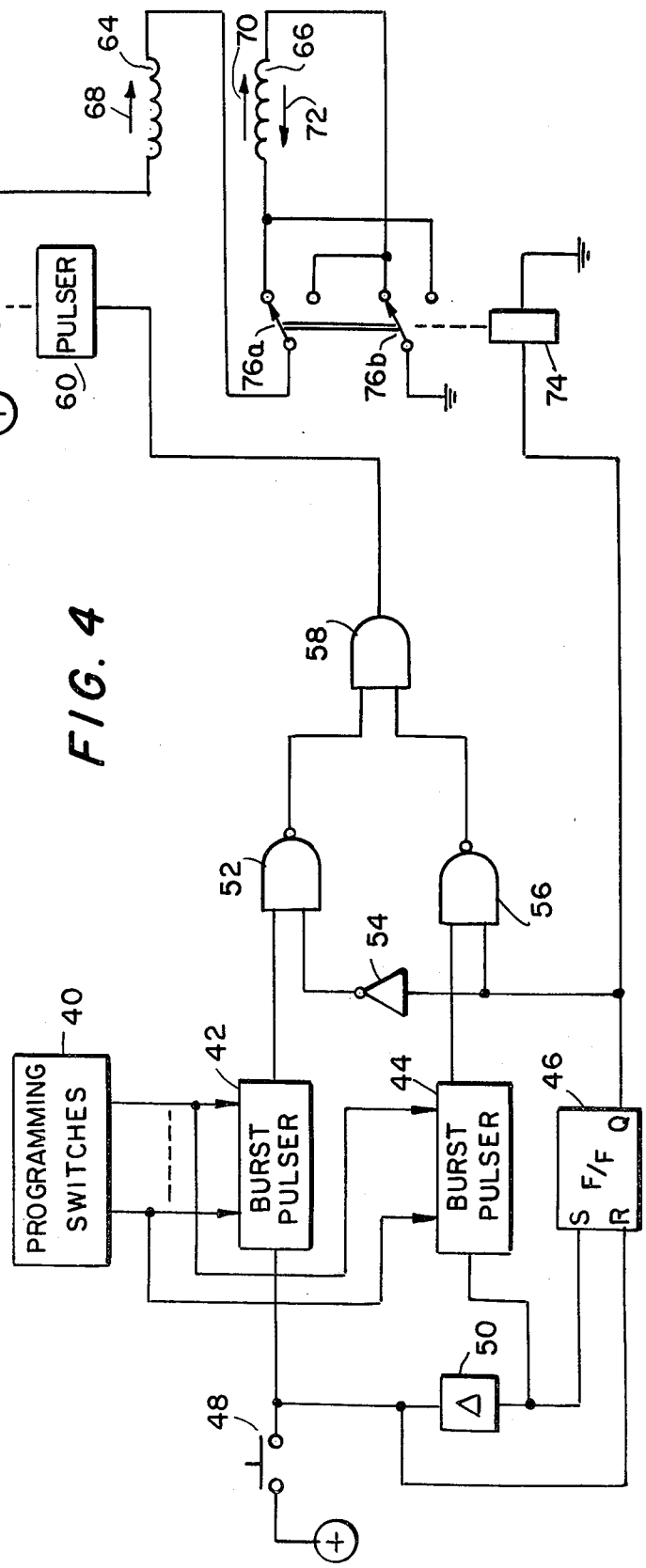

UNIVERSAL PROGRAMMER FOR OPERATING IMPLANTABLE DEVICE REED SWITCH

DESCRIPTION

This invention relates to programmers for use with heart pacers and other programmable medical prostheses, and more particularly to a programmer which can adjust the operating characteristics of different types of prostheses.

It is customary in the heart pacer art to provide a pacer whose operating characteristics such as rate and sensitivity can be adjusted, even following implantation, by operating an external programmer. Typically, the programmer is provided with a magnetic coil which is pulsed in a predetermined sequence in accordance with the new desired parameter values. A reed switch in the pacer opens and closes in accordance with the resulting pulsating flux, and the pacer decodes the reed operations to adjust its operating characteristics, for example, by counting the total number of pulsations. Programmers per se and reed/decoder circuits are well known in the art.

Pacer manufacturers, however, do not all place the reed switch in the same position within their pacers. Even if the pacers have the same overall shape and are placed in the same position within a human body, in one case the axis of the switch might be parallel with the patient's chest in a head-to-toe orientation, and in another case the axis of the reed switch might be perpendicular to the plane of the patient's chest, extending in a front-to-back direction. Each manufacturer therefore provides its own programmer for use with its line of pacers. Even assuming that the programmers of two different manufacturers have the same overall shape and that they are both placed flat on the chest of a patient when they are to be operated, the coils within the programmers generally have different orientations. In one case the axis of the coil, when the programmer is placed on the chest of a patient, will be in the plane of the patient's chest so that the generated flux will be parallel with the patient's chest and pass along the head-to-toe axis of the reed switch within the pacer to be controlled. Another manufacturer, on the other hand, might provide a coil whose axis is perpendicular to the plane of the patient's chest in order that the resulting flux will be directed through a reed switch which has a front-to-back orientation. Even if the pulse sequences for two different types of pacers happen to be the same, it may be necessary to provide two different programmers for adjusting them, the coils of the two different programmers having different orientations. Alternatively, if the same programmer is to be used for both pacers, the physician has to hold it "out of place" by 90 degrees in order to program one of the two pacers, a cumbersome and unreliable procedure.

It is a general object of my invention to provide a programmer for a heart pacer or the like which, while always operated in the same position, can control closure of reeds which may have different orientations in a patient's body. It is another object of my invention to allow use of the same programmer, in the same operating position, with pacers which have not only different reed orientations but also different pulse sequence requirements.

Briefly, in accordance with the principles of my invention and in the illustrative embodiment thereof, the programmer is designed to work with pacers whose reed axes are either vertical within the patient's body or extend through the patient's body from front to back. Flux flows along two paths, the two paths controlling closures of the two differently oriented reeds. Two different pulse burst circuits can be provided, each for generating a pulsating flux sequence for a different one of the two flux paths; each pulsing circuit can control a pulse sequence for a respective type of pacer. In this manner, operation of the programmer can result in pacer adjustments no matter which type of pacer is adjusted (as long as it is a pacer type for which the programmer is designed for use). Preferably, the two pulse sequences, each controlling flux along a respective path, are generated automatically in succession each time that the pacer is operated; in this manner, the physician need not even concern himself with setting a switch on the programmer to identify the particular type of pacer to be programmed. In the case of a programmer designed to adjust two different types of pacers, one of the pulse bursts will have no effect and the other will control reed closures.

Further objects, features and advantages of my invention will become apparent upon consideration of the following detailed description in conjunction with the drawing, in which:

FIG. 1 depicts symbolically a first prior art programmer/pacer reed orientation;

FIG. 2 depicts symbolically a second prior art programmer/pacer reed orientation;

FIG. 3A depicts symbolically the programmer of my invention operating in conjunction with a pacer having a first reed orientation;

FIG. 3B depicts symbolically the programmer of my invention operating in conjunction with a pacer having a second reed orientation; and FIG. 4 depicts schematically the illustrative programmer of my invention.

The numeral 10 in FIG. 1 depicts a prior art programmer. Since the detailed construction of such a programmer is well known to those skilled in the art, all that is shown in FIG. 1, as well as FIGS. 2, 3A and 3B, are the coil and reed orientations necessary for an understanding of the present invention. Programmer 10 has a face 10a which is placed on the chest of the patient. The programmer includes an internal coil 14 which has an orientation such that when the programmer is placed on the chest of a patient, the coil axis is in the head-to-toe direction.

The pacer to be programmed has a reed switch 12, or some other magnetically actuated device, whose operation adjusts the characteristics of the pacer or otherwise effects changes in it. For example, the use of a permanent field to hold the switch closed may disable the pacer operation, while a pulsating field which passes through the switch may control changes in pacer rate, etc. When the pacer is implanted in its recommended position, reed switch 12 also has a head-to-toe orientation. It is thus apparent that when a current flows through coil 14 in the programmer, whether the current be direct or pulsating, the path 16 of the magnetic flux which is generated passes through the reed switch along its axis; a flux in this direction causes the reed to close.

FIG. 2 depicts another conventional arrangement. In this case the implanted pacer includes a reed switch 18 whose axis is in the front-to-back direction. Coil 22 in programmer 20 has a direction such that when face 20a of the programmer is placed on the chest of the patient and a current is made to flow through the coil, the flux which is generated is directed perpendicularly out of the face of the programmer. The resulting flux path 24 passes along the axis of the reed switch.

Each of programmers 10 and 20 is designed for use with pacers (or other medical prostheses) which are contained in one of two groups. A first group includes reed switches, such as switch 12, which are closed when flux passes through them in a head-to-toe direction. The second group includes reed switches, such as switch 18, which are closed when flux passes through them in a front-to-back direction. (It is assumed, of course, that the medical prostheses in both groups are placed in the human body in the same position.) It is apparent that in the examples of FIGS. 1 and 2 the two directions are orthogonal to each other. Because each reed switch responds to flux in one of two orthogonal directions and not to flux in the other, a different programmer must be used for each group of devices—unless the "wrong" programmer is rotated 90 degrees so that its coil faces in the "right" direction for a particular reed switch, a procedure which is hardly recommended. It should be noted that the same remarks apply to devices which are programmed even before implantation, and to devices which are not even implantable; if two devices are held in the same position, two different programmers will be required to program them unless the programmer is held rotated when programming one of the two devices.

As depicted in FIGS. 3A and 3B, the programmer 30 illustrative embodiment of my invention is provided with two parallel coils whose axis are perpendicular to face 30a of the programmer. FIG. 3A depicts programmer 30 operating on prior art reed switch 12 of FIG. 1, and FIG. 3B depicts the programmer operating on prior art reed switch 18 of FIG. 2. In both cases, it is assumed that a current flows through the upper coil such that its left side is a north pole and its right side is a south pole. The current through the lower coil in the two cases, however, is in opposite directions. In the case of the FIG. 3A, the current through the lower coil results in a north pole at the right end and a south pole at the left end. The flux which leaves one coil at one end thus flows directly into the pole of the other coil at the same end, the overall flux path being shown by the numeral 32. It is apparent that the flux path passes through reed switch 12 in a head-to-toe direction to control the reed closure. In the case of FIG. 3B the current through the lower coil causes the left end of the coil to be a north pole and the right end to be a south pole. The fluxes generated by the two coils thus oppose each other and the overall flux follows paths 34a, 34b. It is apparent that the flux from each coil passes through reed switch 18 in a front-to-back direction to control a closure.

Thus simply by controlling the fluxes through the two parallel coils to aid or oppose each other, it is possible to cause the fluxes to follow paths which pass through the reed switches in orthogonal directions. When programming a pacer, for example, pulsating fluxes are required in order to control the opening and closing of a reed switch. This means that current pulses have to flow through each coil so that the flux can pulsate. When programming a pacer which contains a reed switch 12, and assuming that the two coils are wound in the same direction, all that is required is to ensure that any current which flows through the two coils flows through them in opposite directions. When programming a pacer which contains a reed switch 18, the currents must always flow in the same direction through the coils. Of course, if the coils are wound in opposite directions, then the currents in the case of FIG. 3A have to be in the same direction and the currents in the case of FIG. 3B have to be in opposite directions. Each coil is wound on an iron core which exhibits magnetic properties so that when current flows through the coil a large magnetic flux is generated. The key to the operation is that the poles at the ends of the coils on either side of the programmer are the same or opposite, depending upon the orientation of the reed switch which is to be controlled.

With respect to any programmer which utilizes the technique of my invention for generating fluxes which can follow multiple paths, in its most elementary form it may be provided with a switch for selecting between the two paths. After the programming switches are set, as is known in the art, a pulsating current may be caused to flow through the two coils generating poles of the same or opposite type at face 30a of the programmer, depending upon the setting of the switch which controls the selection of the flux path. If the programmer is designed for use with two different types of pacers which require different reed closure sequences to effect programming of the pacers, the programmer may be provided with two pulsing circuits for generating one of two pulse sequences depending upon the setting of the same switch which selects the flux path. In this way, the physician can identify the pacer to be programmed by brand name, e.g., by setting a two-position switch, and then set the programming switches to reflect the desired operating characteristics. When the programmer is operated, not only will the generated flux follow the correct path for the identified pacer, but the pulse sequence for programming that type of pacer will also be the correct sequence.

However, rather than to require the physician to select one of two (or more) possible modes of operation, in the preferred embodiment of my invention the programmer operates in both (or more) modes in succession, so that the physician need not even concern himself with identifying a particular type of pacer by operating a switch on the device. A unit designed, for example, to program the pacers of two different manufacturers, will always program either type of pacer without the physician having to identify one of them. All the physician has to do is to set the programming switches in accordance with the desired operating characteristics and to then press the "start" button. The programming switches set up the desired pulse sequence in each of two burst pulsers, one for each type of pacer. When the programmer is triggered, the first burst pulser operates to generate a pulse sequence which is designed to program one of the two types of pacers in accordance with the settings of the programming switches. When this first pulser operates, the path of the flux which is generated is that which is the correct path for programming the respective type of pacer. Immediately thereafter, the second burst pulser operates and generates a pulse sequence which is designed to program the second type of pacer. When this second burst pulser operates, however, the generated flux follows the other path so that the pacer of the second type can be programmed.

In the circuit of FIG. 4, the numeral 40 represents the programming switches which are manipulated by the physician to adjust the values of various parameters, such as pacer rate, sensitivity, etc. In a conventional programmer these switches control only one type of pulse sequence, but in the illustrative embodiment of the invention the switches control two sequences. Accordingly, the outputs of the programming switches are extended to the inputs of burst pulser 42 and burst pulser 44.

When "start" switch 48 is depressed, the positive potential at the trigger input of burst pulser 42 causes it to generate a series of pulses at its output whose sequence depends on both the setting of programming switches 40 and the format necessary to program a pacer of the first type. After a short delay introduced by delay element 50, burst pulser 44 is triggered and it generates a series of pulses at its output whose sequence depends upon both the setting of programming switches 40 and the format necessary to program a pacer of the second type. The delay of element 50 is sufficient so that pulser 44 begins to operate only after pulser 42 has stopped pulsing.

As soon as switch 48 is operated, the positive potential applied to the reset input of flip-flop 46 causes its Q output to go low. The low potential is applied to one input of NAND gate 56 so that its output remains high to enable one input of gate 58. The low output of the flip-flop is inverted by inverter 54 to enable one input of gate 52. Consequently, it is pulses at the output of pulser 42 which are transmitted through enabled gates 52 and 58 to the input of pulser 60 which controls pulsating currents through coils 64 and 66. Pulser 60 simply follows the pulses at the output of burst pulser 42 to close switch 62, thus causing a current flow through the two coils in accordance with the pulse sequence generated by pulser 42. The directions of the currents through the two coils will be described below.

At the end of the delay introduced by delay element 50, not only is burst pulser 44 triggered, but flip-flop 46 is set since the output of the delay element is connected to the set input of the flip-flop. The Q output now goes high so that inverter 54 causes the output of gate 52 to remain high; thus it is now gates 56 and 58 which are enabled and the pulses extended to pulser 60 are those derived from the output of burst pulser 44. In this way, pulser 60 is controlled to generate two different pulse sequences, for the two types of pacer for which use of the programmer is designed, in two successive parts of an overall pacing cycle.

The flux path during each part of the overall cycle is controlled by the state of flip-flop 46. Whenever pulser 60 causes switch 62 to close, a current flows through coil 64 in the direction of arrow 68. The current then flows through coil 66, in a direction determined by the positions of ganged switches 76a, 76b. The positions of the switches are controlled by relay 74.

During the first part of the overall programming cycle, the Q output of flip-flop 46 is low in potential and relay 74 is not energized. Switches 76a, 76b remain in the positions shown in the drawing, and thus the current which flows through coil 66 flows in the direction of arrow 70. During the second part of the overall programming cycle, when the Q output of flip-flop 46 is high, relay 74 is energized and switches 76a, 76b change positions. The current which now flows through coil 66 is in the direction of arrow 72. With reference to FIGS. 3A and 3B, it will be apparent that during the first half of the overall programming cycle the flux follows the path shown in FIG. 3B (assuming that the coils are wound identically), and during the second half of the cycle the flux follows the path shown in FIG. 3A.

It is thus apparent that in the illustrative embodiment of the invention current pulses through coil 64 are always in the same direction. It is by connecting the right end of coil 64 to different ends of coil 66, during the two halves of each overall cycle of operation, that the current pulses through coil 66 flow in opposite directions.

Although the invention has been described with reference to a particular embodiment, it is to be understood that this embodiment is merely illustrative of the application of the principles of the invention. Numerous modifications may be made therein and other arrangements may be devised without departing from the spirit and scope of the invention.

I claim:

1. A system for generating magnetic flux to control flux-responsive switching in a plurality of medical prostheses to adjust the operating characteristics thereof, such medical prostheses being sensitive to the path of magnetic flux therethrough, a first group of said medical prostheses being responsive to fluxes primarily in a first direction therethrough, and a second group being responsive to fluxes primarily in a second direction therethrough when placed in a human body in the same position as the medical prostheses in said first group; comprising a housing; means within said housing for generating two fluxes having a different paths, each to control flux-responsive switching in medical prostheses in a respective one of said first and second groups when said housing is held in the same orientation relative to the medical prostheses in both groups; and means for selectively controlling the path of the flux which is generated by said flux generating means.

2. A system in accordance with claim 1 wherein said first and second directions are orthogonal to each other.

3. A system in accordance with claim 3 wherein said medical prostheses are heart pacers.

4. A system in accordance with claim 3 wherein any heart pacer in each of said first and second groups has its operating characteristics adjusted responsive to pulsating fluxes therethrough, and said flux generating means generates pulsating fluxes.

5. A system in accordance with claim 4 wherein said flux generating means, during each operation thereof, generates flux first along one path and then along the other to control flux-responsive switching in any heart pacer whose operating characteristics are to be adjusted independent of whether it is contained in said first group of said second group.

6. A system in accordance with claim 5 wherein said flux generating means includes two coils, means for directing a current through each of said coils, and means for selectively controlling the direction of current flow through one of said coils in accordance with the path of the flux which is to be generated.

7. A system in accordance with claim 6 wherein said two coils are oriented in parallel with each other within said housing.

8. A system in accordance with claim 7 wherein said flux generating means causes the same current to flow through both of said coils, and said controlling means connects one end of one coil to a selected end of the other in accordance with the path of the flux which is to be generated.

9. A system in accordance with claim 8 wherein the heart pacers in said first and second groups require different pulsating flux sequences to adjust the operating characteristics thereof, and said flux generating means generates a respective pulsating flux sequence for each flux path.

10. A system in accordance with claim 1 wherein said medical prostheses are heart pacers.

11. A system in accordance with claim 10 wherein any heart pacer in each of said first and second groups has its operating characteristics adjusted responsive to pulsating fluxes therethrough, and said flux generating means generates pulsating fluxes.

12. A system in accordance with claim 11 wherein said flux generating means, during each operation thereof, generates flux first along one path and then along the other to control flux-responsive switching in any heart pacer whose operating characteristics are to be adjusted independent of whether it is contained in said first group or said second group.

13. A system in accordance with claim 12 wherein the heart pacers in said first and second groups require different pulsating flux sequences to adjust the operating characteristics thereof, and said flux generating means generates a respective pulsating flux sequence for each flux path.

14. A system in accordance with claim 1 wherein any medical prosthesis in each of said first and second groups has its operating characteristics adjusted responsive to pulsating fluxes therethrough, and said flux generating means generates pulsating fluxes.

15. A system in accordance with claim 14 wherein said flux generating means, during each operation thereof, generates flux first along one path and then along the other to control flux-responsive switching in any heart pacer whose operating characteristics are to be adjusted independent of whether it is contained in said first group or said second group.

16. A system in accordance with claim 15 wherein the medical prostheses in said first and second groups require different pulsating flux sequences to adjust the operating characteristics thereof, and said flux generating means generates a respective pulsating flux sequence for each flux path.

17. A system in accordance with claim 1 wherein said flux generating means includes two coils, means for directing a current through each of said coils, and means for selectively controlling the direction of current flow through one of said coils in accordance with the path of the flux which is to be generated.

18. A system in accordance with claim 17 wherein said two coils are oriented in parallel with each other within said housing.

19. A system in accordance with claim 18 wherein said flux generating means causes the same current to flow through both of said coils, and said controlling means connects one end of one coil to a selected end of the other in accordance with the path of the flux which is to be generated.

20. A system in accordance with claim 17 wherein the medical prostheses in said first and second groups require different pulsating flux sequences to adjust the operating characteristics thereof, and said flux generating means generates a respective pulsating flux sequence for each flux path.

21. A system in accordance with claim 1 wherein the medical prostheses in said first and second groups require different pulsating flux sequences to adjust the operating characteristics thereof, and said flux generating means generates a respective pulsating flux sequence for each flux path.

* * * * *